United States Patent [19]

Chmiel et al.

[11] Patent Number: 5,384,256
[45] Date of Patent: Jan. 24, 1995

[54] **PECTIN-MODIFIED LIPASE FROM *MUCOR JAVANICUS* WITH LOWERED SATURATED/UNSATURATED FATTY ACID RATIO**

[75] Inventors: Oliver Chmiel, Lausanne; Helmut Traitler, Corseaux, both of Switzerland

[73] Assignee: Nestec S.A., Vevey, Switzerland

[21] Appl. No.: 43,357

[22] Filed: Apr. 6, 1993

[30] Foreign Application Priority Data

Apr. 25, 1992 [EP] European Pat. Off. ........... 92107094

[51] Int. Cl.$^6$ ................. C12N 9/22; C12N 11/10; C12N 11/08; C12N 9/96
[52] U.S. Cl. .................. 435/198; 435/178; 435/180; 435/188
[58] Field of Search ............ 435/188, 198, 134, 178, 435/180, 174

[56] References Cited

U.S. PATENT DOCUMENTS

| | | | |
|---|---|---|---|
| 4,065,580 | 12/1977 | Feldman et al. | 426/33 |
| 4,250,267 | 2/1981 | Hartdegen | 435/317.1 |
| 4,464,468 | 8/1984 | Avrameas et al. | 435/177 |
| 4,572,897 | 2/1986 | Amotz et al. | 435/177 |
| 4,645,741 | 2/1987 | Inada | 435/134 |
| 4,663,287 | 5/1987 | Barker | 435/188 |
| 4,766,106 | 8/1988 | Katre et al. | 514/12 |
| 4,814,098 | 5/1989 | Inada et al. | 252/62.51 |
| 4,894,339 | 1/1990 | Hanazato et al. | 435/182 |
| 5,108,916 | 4/1992 | Cobbs et al. | 435/135 |

FOREIGN PATENT DOCUMENTS

A20149520 7/1985 European Pat. Off. .
1174854 12/1969 United Kingdom .
WO8902916 4/1989 WIPO .

OTHER PUBLICATIONS

Brown et al. (1973) *Biotech. Bioeng.*, 15, 359–375.
Johri, et al., "Lipase from Sporotrichum (Chrysosporium) Thermophile Apinis: Production and Characteristics of Free and Immobilized Enzyme" (1991).
Database WPIL Derwent Publications Ltd. AN85-156198 (1985).
Huge–Jensen, et al., "Studies On Free and Immobilized Lipases from Mucor Miehei." J. Am. Oil Chem. Soc., vol. 65, No. 6 (Jun. 1988) pp. 905–910.
Jensen et al., "Selectivity is an Important Characteristic of Lipases (Acylglycerol Hydrolases) Biocatalysis," 1990, vol. 3 pp. 307–316.
Johri, et al., "Lipase From Sportotrichum (Chrysosporium) Thermophile Apinis Production DND Characteristics of Free and Immobilized Enzyme" J. Microb. Biotechnol., vol. 6 (2), 44–57, (1991).

*Primary Examiner*—Douglas W. Robinson
*Assistant Examiner*—Jon P. Weber
*Attorney, Agent, or Firm*—Vogt & O'Donnell

[57] ABSTRACT

A native lipase from *Mucor javanicus* is modified by bonding it to a pectin. The pectin-modified lipase releases fatty acids of identical chain length from a lipidic substrate in a lower saturated-to-unsaturated fatty acid ratio than the native, unmodified, lipase.

10 Claims, No Drawings

PECTIN-MODIFIED LIPASE FROM *MUCOR JAVANICUS* WITH LOWERED SATURATED/UNSATURATED FATTY ACID RATIO

BACKGROUND OF THE INVENTION

This invention relates to a modified lipase, to a process for modifying a lipase and to the uses of a lipase thus modified for nutritional and flavouring purposes.

Lipases are enzymes which are capable of hydrolyzing or esterifying emulsified fats. During this process, the fatty acids are released from the tri-, di- and monoglycerides. A lipase has its own specificity according to its type and origin. This may be a regio-specificity, for example in the case of a lipase of *Mucor miehei* which selectively cleaves the fatty acids in positions 1 and 3 of the glyceride, or a specificity for the substrate, as for example in the case of a lipase of *Geotrichum candidum*, or even a mixed specificity resulting from the two preceding properties.

Attempts have been made to change the natural properties of lipases by chemical modification to give them better solubility in organic solvents (cf, for example European patent Application Publication No.-149 520) with a view to improving their hydrolysis and synthesis activities in transesterification reactions in organic medium.

SUMMARY OF THE INVENTION

It has now surprisingly been found that the specificity of a lipase with respect to lipidic substrates can be influenced by subjecting it to physico-chemical modification.

Accordingly, the present invention relates to a lipase specific with respect to lipidic substrates which has been modified from a native lipase, characterized in that, in relation to the starting lipase, it has a polarity induced by bonding to an oligomer or polymer.

The present invention also relates to a process for modifying a lipase to change its specificity with respect to lipidic substrates, characterized in that the lipase is reacted with an oligomer or with a polymer of which the polarity is selected to promote the release of fatty acids having a predetermined degree of saturation without modifying its specificity with respect to the chain length of the fatty acids released.

DETAILED DESCRIPTION OF THE INVENTION

According to the invention, a preferred lipase, MAP-10®  of *Mucor javanicus*, belongs to the second category mentioned above and has a substrate specificity for medium-chain and long-chain fatty acids.

To modify the lipase, it is reacted with an oligomer or a polymer (hereinafter, the term polymer is used to denote both an oligomer and a polymer as such), which may optionally have been activated, which has a molecular weight of preferably 500 to $10^6$ and of which the polarity extends from the absence of polarity to a value of the order of 1000 McReynolds. The McReynolds polarity scale (McReynolds, W. O., J. Chromatogr. Sci. 8, 685 (1970)) may be defined on the basis of the gas phase chromatography retention indices of five solvents of different polarity as measured on a polymer used as stationary phase in a gas phase chromatography column which gives an evaluation of the polarity of the polymer tested by comparison with squalane (saturated C30 hydrocarbon obtained by hydrogenation of squalene) to which a polarity value of 0 is attributed by definition.

The polymers used may vary in their chemical nature and may be of synthetic origin or, preferably, natural origin. They include, for example, dimethyl polysiloxanes and polyethylene glycols grafted with polar groups or, preferably, pectins which have the advantage of already possessing polar carboxyl groups in their structure. Polymers of natural origin also include proteins, for example β-casein, lactoglobulin, albumin, lactalbumin, and polypeptides, for example poly-L-leucine, poly-L-glutamic acid and poly-L-lysine. The proteins or polypeptides are used in the form of an aqueous solution containing, for example, 1 to 40 mg protein/polypeptide per ml. In the case of the grafted polymers, grafting may be carried out by activating the polymer by reaction with a monomeric coupling agent bearing difunctional polar groups, for example in the case of polysiloxanes with a glycidoxypropyl trimethoxysilane in the presence of a compound initiating a radical reaction, for example dicumyl peroxide, or in the case of a polyethylene glycol, for example, with the chloride of hydrocyanic acid in the presence of a solvent.

The polymer thus modified in its polarity is then reacted with the enzyme under strongly basic pH conditions in the case of polysiloxanes or polyethylene glycols or under mildly acidic pH conditions in the case of pectins, after which the treated enzyme is dried, for example by freeze drying, with a view to subsequent use.

It has been found that the natural specificity of the enzyme thus transformed, for example in the case of the lipase of *Mucor javanicus* which—in the native state—specifically releases the medium chain and long chain fatty acids, was retained in the modified enzyme. By contrast, the saturated-to-unsaturated ratio of the long chain fatty acids of the same chain length released by hydrolysis changed with the polarity of the reactant formed by the polymer in relation to that obtained with the native enzyme. Thus, an increase in the polarity of the polymer resulted in a displacement of the fatty acids released towards the unsaturated fatty acids. Conversely, treatment of the enzyme with an apolar polymer resulted in the preferential release of saturated fatty acids of equal chain length. This surprising phenomenon of influence by the external route of the specificity of the enzyme can be utilized in various applications in the food industry.

Accordingly, the present invention also relates to a process for flavouring a food product, characterized in that a substrate incubated with a lipase modified by the process according to the invention is incorporated in the product in question or in that the product in question is treated with a lipase modified by the process according to the invention.

The present invention also relates to a process for improving the nutritional qualities of a lipidic substrate, characterized in that a fat is treated with a modified apolar lipase, i.e. a lipase increased in polarity in order preferably to release the saturated fatty acids in a first step, and the substrate is treated with a modified polar lipase in a second step so that the unsaturated fatty acids are preferentially introduced into the fat by transesterification. The result of this is to increase the value of the fat from the point of view of nutritional physiology. The advantage of this method is that it is possible to transform a substrate from a native lipase of the same origin, for example of food quality, in a process involving several steps.

Alternatively, the property of modifying a specific enzyme which preferentially releases short-chain fatty acids may be utilized, for example, in the production of cheese by accelerating the ripening process, for example to produce specific flavours. An enzyme of the type in question may thus be modified as required, for example without having to resort to genetic modification of the microorganism producing the enzyme. In addition, by preferentially releasing long-chain unsaturated fatty acids by the action of a suitably modified enzyme, it is possible to produce flavour precursors because it is known that the oxidation and degradation products of these fatty acids, for example alcohols, alkanes, aldehydes, ketones and esters, are flavours. For example, it is possible in this way to produce a milk chocolate with a "crumb" flavour as described in applicants' co-pending patent application European Patent Application No. 92107095.9 filed under the title "A process for flavouring a milk chocolate". The enzymes may of course be used as such in solution or in suspension in the substrate or may be fixed to a support.

EXAMPLES

The invention is illustrated by the following Examples, in which parts and percentages are by weight unless otherwise indicated.

Example 1

2 g dimethyl polysiloxane having a molecular weight of approximately $10^6$ (SE-30 ®), 1 g difunctional monomeric silane (glycidoxypropoxysilane, A-187 ®) and 30 mg dicumyl peroxide are dissolved in 150 ml chloroform and, after heating, the mixture is kept under reflux for 2 h. The polymer used has a polarity of 44 on the McReynolds scale, i.e. it is substantially apolar. The solvent is then evaporated and the residue is taken up in 200 ml of a 0.1M aqueous buffer solution of sodium tetroxide borate having a pH of 9. 0.2 g lipase of *Mucor javanicus* (MAP-10 ®, a product of AMANO) is then added and the mixture is stirred for 1 hour under nitrogen at ambient temperature. On completion of the reaction, the pH is adjusted to 7 by addition of concentrated hydrochloric acid, after which the solution is concentrated by ultrafiltration and the concentrate is freeze-dried.

Example 2

30 g monomethoxy polyethylene glycol having a molecular weight of approximately 1500 (PEG-1540, Carbowax ®) are dissolved in 200 ml toluene in the presence of 12 g of a molecular sieve and 12 g sodium carbonate. The polymer is then activated by reaction with 0.8 g chloride of hydrocyanic acid with stirring for 2 h at 80° C. After cooling, the reaction medium is filtered and is then taken up in petroleum ether and the activated polymer is recovered. It has a polarity of 554 on the McReynolds scale. 0.2 g activated monomethoxypolyethylene glycol and 0.2 g lipase MAP-10 ® are dissolved in 250 ml of a 0.1M aqueous buffer solution of sodium tetroxide borate having a pH of 10, after which the solution is stirred under nitrogen for 1 h at ambient temperature. On completion of the reaction, the solution is adjusted to pH 7 by addition of concentrated hydrochloric acid, after which the solution is dialyzed and then freeze-dried.

Example 3

3 g dicyanoethyl polysiloxane having a molecular weight of $10^5$ to $10^6$ (OV-275), 1 g of difunctional monomeric silane (glycidoxypropoxysilane, A-187) and 45 ml dicumyl peroxide are dissolved in 200 ml acetone and the resulting solution is heated and kept under reflux for 3 h. The polymer has a polarity of 844 on the McReynolds scale. After evaporation of the solvent, the residue is taken up in 150 ml acetone, after which a solution of 0.2 g lipase MAP-10 in 25 ml aqueous buffer of pH 9 containing 0.1M sodium tetroxide borate is added and the solution is stirred under nitrogen for 1 h at ambient temperature. On completion of the reaction, the pH is adjusted to 7 by addition of concentrated hydrochloric acid, after which the solution is freeze-dried.

Example 4

1 g apple pectin A having a molecular weight of $10^5$ -$1.5 \cdot 10^5$ (10% methylated) and 0.2 g lipase MAP-10 are mixed in aqueous solution at pH 5 and the solution is stirred under nitrogen for 1 hour at ambient temperature. The polymer is highly polar. The non-solubilized pectin is then carefully separated by centrifugation, after which the pH value of the solution is adjusted to 7 by addition of a base, the solution is concentrated by ultrafiltration and the concentrate is freeze-dried.

Example 5

The modified enzymes of the preceding Examples are used for the lipolysis of milk. To this end, whole milk is incubated with 0.5 U/ml lipase for 30 mins. at 37° C. After the reaction, the substrate is taken up while stirring in 4 times its volume of a mixture of equal volumes of chloroform and methanol, followed by centrifugation for 10 minutes. The organic phase is then collected and applied to thin-layer chromatography plates, after which the free fatty acids are separated from the other compounds and their isopropyl esters are formed by esterification. The isopropyl esters are then quantitatively analyzed by gas phase chromatography. The lipolysis results are set out in Table 1 below in the form of the ratio between the quantities released of palmitic acid (C 16:0) oleic acid (C 18:1) and linoleic acid (C 18:2), respectively, and the corresponding quantity of stearic acid (C 18:0) released.

TABLE 1

| Polymer by increasing polarity | Ratio between the quantities of fatty acids released | | |
|---|---|---|---|
| | C 16:0 / C 18:0 | C 18:1 / C 18:0 | C 18:2 / C 18:0 |
| Example 1 | 2.57 | 1.59 | 0.15 |
| Example 2 | 3.93 | 1.45 | 0.05 |
| Example 3 | 3.78 | 4.43 | 2.07 |
| Example 4 | 3.43 | 5.08 | 0.22 |
| Native lipase | 3.15 | 2.45 | 0.14 |

A change is observed in the proportions of the fatty acids released by the modified enzymes by comparison with those of the fatty acids released by the native enzyme in the form of a substantial increase in the unsaturated fatty acids of identical chain length.

Examples 6-12

0.2 g lipase MAP-10 are dissolved in 10 ml of an aqueous solution containing 200 mg of the proteins and polypeptides shown below. The enzyme is then stirred for 1 hour in the presence of the substrate. The enzymatic preparation is then introduced into a stable mixture of emulsions based on tristearin and triolein and incubated as described in Example 5. The fatty acids released were isolated and identified in the same way as in Example 5. The results obtained are set out in Table 2 below where they are expressed in the form of the ratio by weight of oleic acid to stearic acid.

TABLE 2

|  | Ratio of C 18:1 to C 18:0 |
|---|---|
| Untreated lipase | 2.9 |
| Example 6: beta-casein | 6.3 |
| Example 7: lactoglobulin | 5.5 |
| Example 8: albumin | 3.8 |
| Example 9: lactalbumin | 4 |
| Example 10: poly-L-glutamic acid | 4.4 |
| Example 11: poly-L-lysine | 3.9 |
| Example 12: poly-L-leucine | 2.4 |

Example 13

The effects of lipolysis by the action of the native lipase MAP-10 (3) and the modified lipase according to Example 4 (2) were tested under the same incubation conditions on an instant fresh cheese reconstituted from 70 g powder in 210 ml water by comparison with the standard cheese (1) in blind tasting tests. Lipolysis was carried out by addition of 30 mg enzyme solubilized in 5 ml water to 70 g cheese reconstituted in 205 ml water and incubation for 30 minutes at ambient temperature. The cheeses were then cooled to approximately 8°–10° C. Cheese (2) had a cheese taste similar to and more intense than that of (1), but without the emission of the bad odours or the old taste obtained with (3). The average taste scores were 6 for (1), 7.6 for (2) and 8.8 for (3) (0=best score, 10=worst score).

Example 14

To produce cheese sauces with the taste of Cheddar, an ultrafiltered whole milk concentrate lipolyzed either by the native lipase MAP-10 (b) or by the modified lipase according to Example 4 (c) was incorporated as partial replacement of the Cheddar in the standard formula (a). The ultrafiltered milk was incubated with the lipases for 24 h at 50° C. The composition of the sauces is shown in Table 3 below.

TABLE 3

| Ingredient | Concentration (%) | | |
|---|---|---|---|
| Water | 68.05 | 68 | 69.35 |

TABLE 3-continued

| Ingredient | Concentration (%) | | |
|---|---|---|---|
| Cheddar | 10 | 6 | 6 |
| Lipolyzed concentrate (b) | — | 4 | — |
| Lipolyzed concentrate (c) | — | — | 4 |
| Cheddar flavour | 0.8 | 0.8 | — |
| Cornstarches | 13.8 | 13.8 | 13.8 |
| Soybean oil | 3.9 | 3.9 | 3.9 |
| Salts, colourants, thickeners | Balance to 100 | | |
| Taste score | 2.8 | 1.8 | 1.4 |

(0 = best, 10 = worst)

Compared with the standard sauce (a), the sauce containing the concentrate lipolyzed with the native lipase (b) had a pronounced odour and taste of Cheddar while the sauce containing the concentrate lipolyzed with the modified lipase (c) had a slight and agreeable butyric note and a slight and agreeable taste of walnuts.

We claim:

1. A process for modifying a native lipase comprising the steps of mixing the native lipase, which is obtained from *Mucor javanicus* and which has a medium-chain and long-chain fatty acid substrate specificity, with pectin in an acidic aqueous solution to bind the lipase to the pectin, separating non-solubilized pectin from the aqueous solution, and recovering the solution containing the lipase bound to the pectin.

2. A process according to claim 1 wherein the pectin has a molecular weight of $1 \times 10^5$ to $1.5 \times 10^5$.

3. A process according to claim 1 further comprising neutralizing the aqueous solution from which non-solubilized pectin has been removed and concentrating the neutralized solution to obtain a modified lipase concentrate.

4. A process according to claim 3 wherein the neutralized solution is ultrafiltered to concentrate the solution.

5. A process according to claim 3 further comprising drying the concentrate to obtain a dried modified lipase.

6. A process according to claim 5 wherein the concentrate is freeze dried.

7. A product obtained from the process of claim 1.

8. A product obtained from the process of claim 3.

9. A product obtained from the process of claim 5.

10. A modified lipase comprising a lipase, which is obtained from *Mucor javanicus* and which has a medium-chain and long-chain fatty acid substrate specificity, bonded to pectin, wherein the modified lipase releases fatty acids of identical chain length from a lipidic substrate but in a lower saturated to unsaturated ratio compared to the lipase when it is unmodified native lipase.

* * * * *